United States Patent
Joseph et al.

(10) Patent No.: US 9,375,261 B2
(45) Date of Patent: Jun. 28, 2016

(54) LIMITED-USE MEDICAL DEVICE

(71) Applicant: COVIDIEN LP, Mansfield, MA (US)

(72) Inventors: Daniel A. Joseph, Golden, CO (US); Leslie M. Joseph, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 175 days.

(21) Appl. No.: 14/085,943

(22) Filed: Nov. 21, 2013

(65) Prior Publication Data

US 2014/0200580 A1 Jul. 17, 2014

Related U.S. Application Data

(60) Provisional application No. 61/753,604, filed on Jan. 17, 2013.

(51) Int. Cl.

| A61B 18/18 | (2006.01) |
|---|---|
| A61B 18/14 | (2006.01) |
| *A61L 2/00* | (2006.01) |
| *A61L 2/02* | (2006.01) |
| *A61L 2/04* | (2006.01) |
| *A61L 2/16* | (2006.01) |
| A61L 2/07 | (2006.01) |
| A61L 2/18 | (2006.01) |
| A61L 2/20 | (2006.01) |
| A61B 19/00 | (2006.01) |

(52) U.S. Cl.
CPC ............ *A61B 18/1445* (2013.01); *A61L 2/00* (2013.01); *A61L 2/02* (2013.01); *A61L 2/04* (2013.01); *A61L 2/16* (2013.01); *A61B 2018/1455* (2013.01); *A61B 2019/4873* (2013.01); *A61L 2/07* (2013.01); *A61L 2/18* (2013.01); *A61L 2/202* (2013.01); *A61L 2/204* (2013.01); *A61L 2/206* (2013.01); *A61L 2202/24* (2013.01)

(58) Field of Classification Search
CPC .................. A61B 18/1445; A61B 2018/1455; A61B 2019/4873; A61L 2202/24; A61L 2/00; A61L 2/02; A61L 2/04; A61L 2/07; A61L 2/16; A61L 2/18; A61L 2/202; A61L 2/204; A61L 2/206
See application file for complete search history.

(56) References Cited

U.S. PATENT DOCUMENTS

| 5,313,935 | A | * | 5/1994 | Kortenbach et al. | 600/117 |
|---|---|---|---|---|---|
| 5,991,355 | A | * | 11/1999 | Dahlke | 377/15 |
| 6,387,092 | B1 | * | 5/2002 | Burnside et al. | 606/32 |
| 8,998,799 | B2 | * | 4/2015 | Orban et al. | 600/130 |
| 2002/0165549 | A1 | | 11/2002 | Owusu-Akyaw et al. | |
| 2003/0208196 | A1 | * | 11/2003 | Stone | 606/41 |
| 2005/0021025 | A1 | * | 1/2005 | Buysse et al. | 606/51 |
| 2007/0215001 | A1 | * | 9/2007 | Voegele | 106/31.01 |

(Continued)

OTHER PUBLICATIONS

U.S. Appl. No. 08/926,869, filed Sep. 10, 1997, James G. Chandler.

(Continued)

*Primary Examiner* — Michael Peffley
*Assistant Examiner* — Amanda Zink

(57) ABSTRACT

A medical device may include one or more operable components and one or more limited-use portions. The limited-use portion(s) is configured to transition from a first state to a second state upon being subjected to sterilization above a sterilization threshold. In the second state, the limited-use portion(s) inhibit the operability of the one or more operable components.

18 Claims, 12 Drawing Sheets

(56) References Cited

U.S. PATENT DOCUMENTS

| | | | |
|---|---|---|---|
| 2013/0289559 A1* | 10/2013 | Reid, Jr. | A61B 18/1477 606/41 |
| 2014/0060161 A1* | 3/2014 | Schick et al. | 73/53.01 |

OTHER PUBLICATIONS

U.S. Appl. No. 09/177,950, filed Oct. 23, 1998, Randel A. Frazier.
U.S. Appl. No. 09/387,883, filed Sep. 1, 1999, Schmaltz, et al.
U.S. Appl. No. 09/591,328, filed Jun. 9, 2000, Ryan, et al.
U.S. Appl. No. 12/336,970, filed Dec. 17, 2008, Sremcich, et al.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13-838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.

* cited by examiner

LIMITED-USE MEDICAL DEVICE

CROSS REFERENCE TO RELATED APPLICATION

The present application claims the benefit of and priority to U.S. Provisional Application Ser. No. 61/753,604, filed on Jan. 17, 2013, the entire contents of which are incorporated herein by reference.

BACKGROUND

1. Technical Field

The present disclosure relates to medical devices. More particularly, the present disclosure is directed to limited-use medical devices and medical devices including limited-use portions.

2. Background of the Related Art

Certain medical devices (or components thereof) are capable of being used multiple times, and are thus referred to as reusable devices (or reusable components), while other medical devices (or components thereof) are configured for single use, and are thus referred to as disposable devices (or disposable components). Many such reusable and disposable medical devices, and/or the components thereof, are designed for a pre-determined number of uses and/or for a pre-determined usage time. Use of these devices beyond their prescribed usage time or number of uses may result in failure of the device, damage to the device or surrounds, and/or injury to the patient or clinician. On the other hand, given the rising costs of performing medical procedures, clinician's have an incentive to maximize the reuse of medical devices (or components thereof).

SUMMARY

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the tem "distal" refers to the end of the apparatus that is farther away from the user. The term "clinician" refers to any medical professional (e.g., doctor, surgeon, nurse, or the like) performing a medical procedure. To the extent consistent, any of the aspects and features described herein may be used in conjunction with any or all of the other aspects and features described herein.

In accordance with the present disclosure, a medical device is provided including one or more operable components, and one or more limited-use portions. The limited-use portions are configured to transition from a first state to a second state upon being subjected to sterilization above a sterilization threshold. In the second state, the limited-use portion(s) inhibit the operability of one or more of the operable components, thereby rendering the medical device inoperable.

In one aspect, sterilization of the limited-use portion above the sterilization threshold renders the medical device mechanically inoperable.

In another aspect, sterilization of the limited-use portion above the sterilization threshold renders the medical device electrically inoperable.

In another aspect, sterilization includes use of a chemical sterilization process. In such aspects, the limited-use portion is sensitive to one or more of the chemicals used in the chemical sterilization process.

In another aspect, the chemical sterilization process includes the use of one or more chemical sterilizers, e.g., hydrogen peroxide, water, saline, alcohol, ethylene oxide, ozone, bleach, chlorine, glutaraldehyde, formaldehyde, phthalaldehyde, silver, triclosan, and/or combinations thereof. The limited-use portion transitions to the second state due to contact with one or more of these chemical sterilizers.

In another aspect, sterilization includes use of an autoclave. In such aspects, the limited-use portion transitions to the second state due to autoclaving.

In another aspect, sterilization includes the use of an energy-based sterilization process. In such aspects, the limited-use portion transitions to the second state due to exposure to the energy-based sterilization process.

In another aspect, sterilization includes a high temperature sterilization process having a sterilization temperature. In such aspects, the limited-use portion transitions to the second state at a temperature equal to or below the sterilization temperature.

In another aspect, the limited-use portion further includes one or more temperature fuses connected to one or more electrical components thereof. The temperature fuse is configured to transition to the second state at a temperature equal to or below the sterilization temperature.

In another aspect, the medical device includes a housing, a pair of jaws for clamping tissue, a pivot pin rotatably connecting the jaws, and at least one electrode connected to said jaws for applying energy to tissue. In such aspects, the housing, jaws, pivot pin, and/or electrode include a limited-use portion.

A method provided in accordance with aspects of the present disclosure includes providing a medical device including one or more operable components and one or more limited-use portions. The method further includes subjecting the medical device to sterilization above a sterilization threshold, thereby transitioning the limited-use portion from a first state to a second state. In the second state, the limited-use portion inhibits the operability of one or more of the operable components, thereby rendering the medical device inoperable. The method may further include any of the features described above with respect to the previous aspects.

BRIEF DESCRIPTION OF THE DRAWINGS

The above and other aspects, features, and advantages of the present disclosure will become more apparent in light of the following detailed description when taken in conjunction with the accompanying drawings, wherein.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
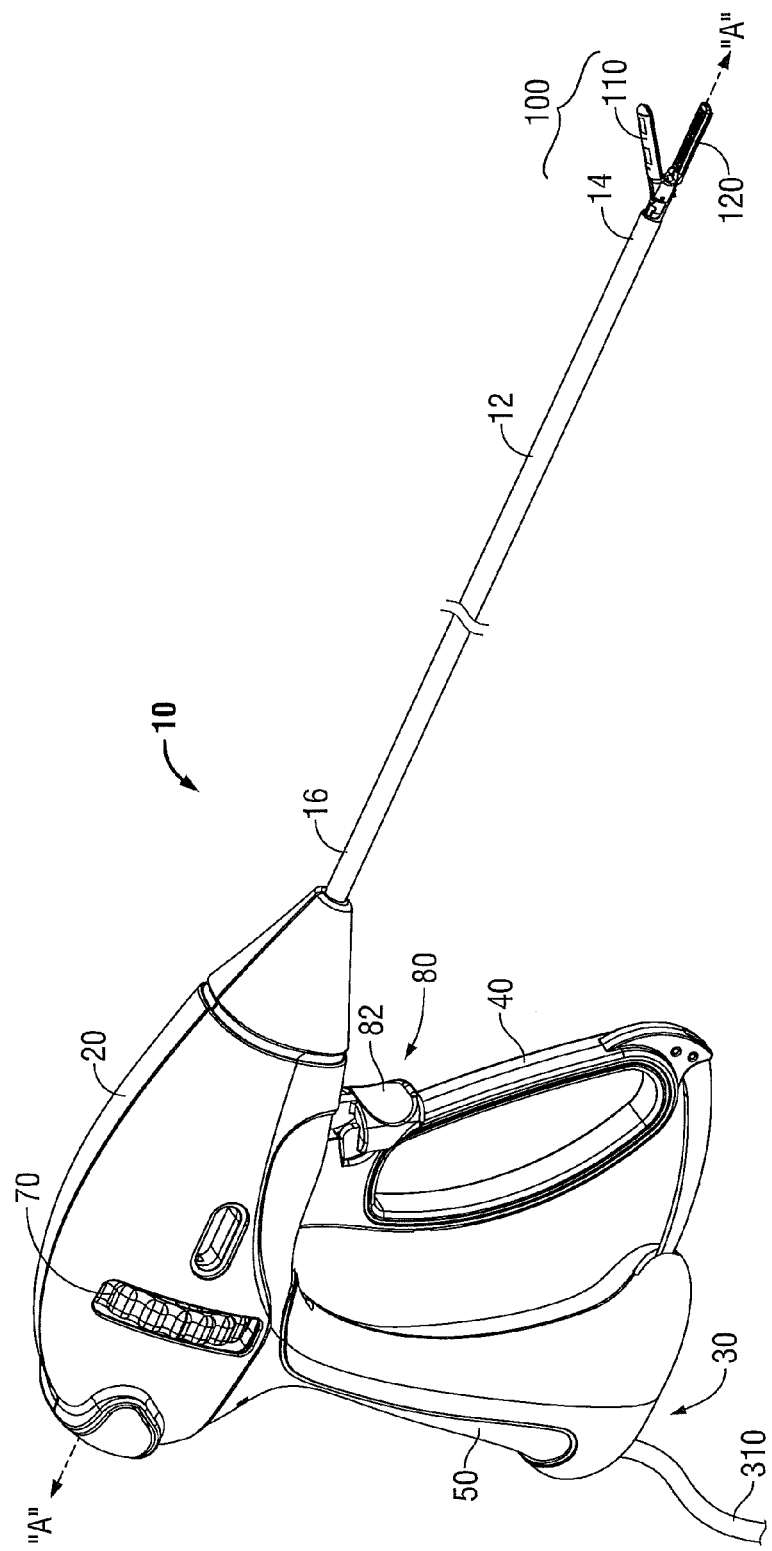
FIG. 1 is a perspective view of a medical device provided in accordance with the present disclosure.

Referring now to FIG. 1, a forceps 10 for use in connection with endoscopic surgical procedures is shown, although forceps 10 may also be configured for use in connection with traditional open surgical procedures. Alternatively, the present disclosure may be embodied in any other suitable medical devices such as, but not limited to scissors, staplers, implants, probes, syringes, and any other electrical, mechanical, or electromechanical medical devices.

Continuing with reference to FIG. 1, forceps 10 defines a longitudinal axis "A-A" and includes a housing 20, a handle assembly 30, a rotating assembly 70, a trigger assembly 80 and an end effector assembly 100. End effector assembly 100 includes first and second jaw members 110, 120, respectively, configured to pivot relative to one another between a spaced-apart position and an approximated position for grasping tissue therebetween. Forceps 10 further includes a shaft 12 having a distal end 14 configured to mechanically engage end effector assembly 100 and a proximal end 16 that mechanically engages housing 20. Forceps 10 also includes a cable 310 that connects forceps 10 to a generator (not shown) or other suitable power source, although forceps 10 may alternatively be configured as a battery powered instrument. Cable 310 includes wires 311 (FIGS. 3C-3D) extending therethrough and into housing 20 to ultimately connect the source of energy (not explicitly shown) to tissue-contacting surfaces 216, 226 (FIG. 2) of jaw members 110, 120, respectively, to conduct energy therebetween and through tissue grasped between jaw members 110, 120 to treat tissue.

With continued reference to FIG. 1, handle assembly 30 includes a fixed handle 50 and a moveable handle 40. Fixed handle 50 is integrally associated with housing 20 and handle 40 is moveable relative to fixed handle 50. Rotating assembly 70 is rotatable in either direction about a longitudinal axis "A-A" to rotate end effector 100 about longitudinal axis "A-A." The housing 20 houses the internal working components of the forceps 10.

Figure 2:
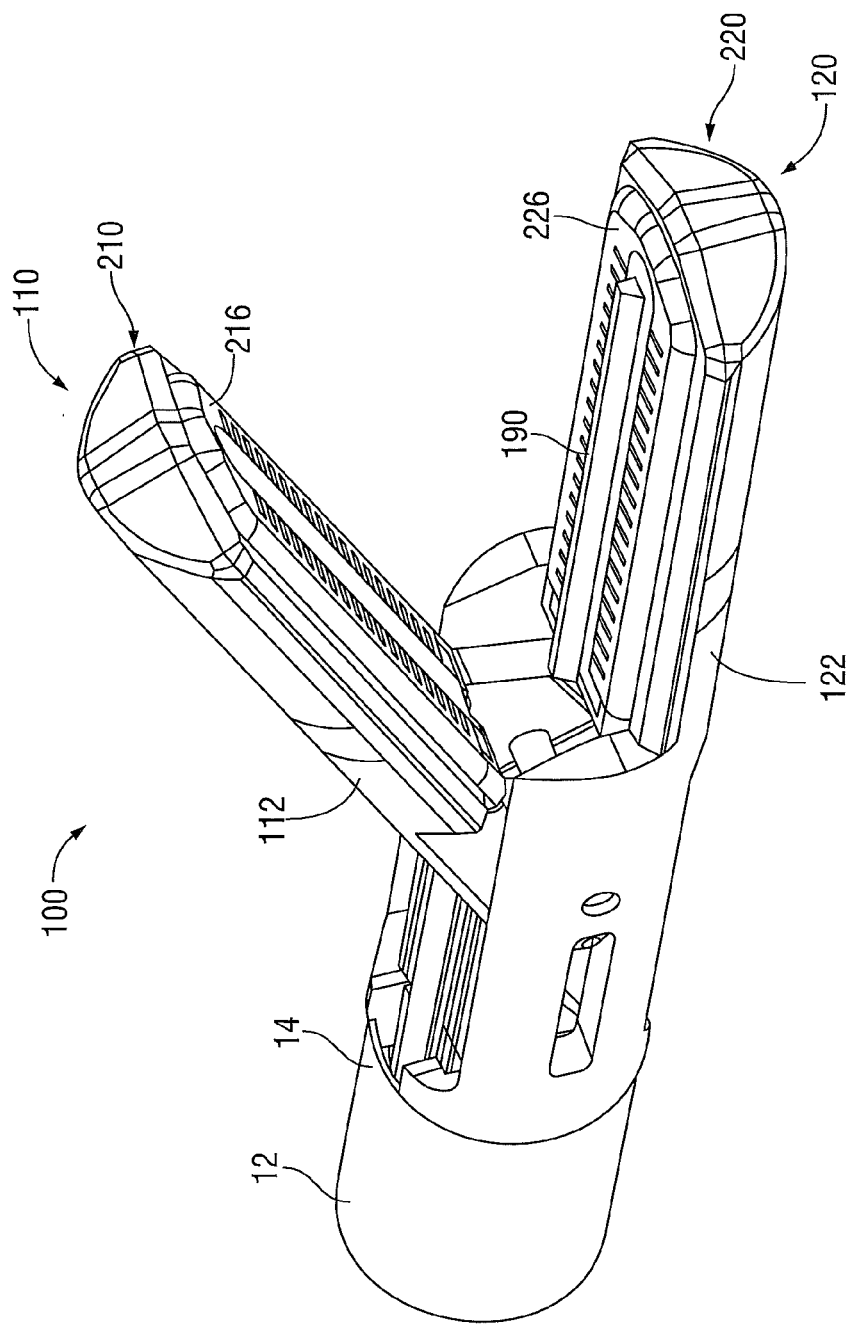
FIG. 2 is a perspective view of an end effector assembly provided in accordance with the present disclosure and configured for use with the medical device of FIG. 1.

Referring FIG. 2, end effector assembly 100 is shown attached at a distal end 14 of shaft 12 and includes a pair of opposing jaw members 110 and 120. Each of the first and second jaw members 110, 120 includes a fixed jaw frame 112, 122, respectively, and a replaceable component 210, 220, respectively, selectively engagable with the respective jaw frame 112, 122 to form the fully assembled jaw members 110, 120, respectively. However, jaw members 110, 120 of end effector assembly 100 may also be configured as integral components, e.g., wherein components 210, 220 are fixedly engaged or otherwise integrated with jaw frames 112, 122 of jaw members 110, 120, respectively.

End effector assembly 100 is designed as a unilateral assembly, i.e., where jaw member 120 is fixed relative to shaft 12 and jaw member 110 is moveable relative to both shaft 12 and fixed jaw member 120. However, end effector assembly 100 may alternatively be configured as a bilateral assembly, i.e., where both jaw member 110 and jaw member 120 are moveable relative to one another and with respect to shaft 12.

Each jaw member 110, 120 defines an electrically conductive tissue-contacting surface 216, 226 configured to connect to the energy source (not shown), e.g., via wires 311 (FIGS. 3C-3D) of cable 310 (FIG. 1), for conducting energy therebetween and through tissue grasped between jaw members 110, 120 to treat tissue. In some embodiments, a knife assembly (not shown) is disposed within shaft 12 and a knife channel (not shown) is defined within one or both of jaw members 110, 120, respectively, to permit reciprocation of a knife blade (not shown) therethrough for mechanically cutting tissue grasped between jaw members 110, 120. In such an embodiment, trigger 82 of trigger assembly 80 (see FIG. 1) is operable to advance the knife blade (not shown) between a retracted position, wherein the knife blade (not shown) is disposed within shaft 12, and an extended position, wherein the knife blade (not shown) extends between jaw members 110, 120 to cut tissue grasped therebetween. Alternatively, end effector assembly 100 may be adapted for electrical cutting via an electrical cutting insert 190 connected to the source of energy (not shown), e.g., via wires 311 (FIGS. 3C-3D) of cable 310 (FIG. 1), thus obviating the need for a knife assembly (not shown). Further, end effector assembly 100 may be adapted for both mechanical cutting and electrical cutting, thus allowing a user to select a mode of operation best suited for the particular surgical procedure to be performed.

Referring again to FIG. 1, moveable handle 40 of handle assembly 30 is ultimately connected to a drive assembly 140 (FIGS. 3C-3D) that, together, mechanically cooperate to impart movement of jaw members 110 and 120 between a spaced-apart position and an approximated position to grasp tissue between tissue-contacting surfaces 216 and 226 of jaw members 110, 120, respectively. As shown in FIG. 1, moveable handle 40 is initially spaced-apart from fixed handle 50 and, correspondingly, jaw members 110, 120 are disposed in the spaced-apart position. Moveable handle 40 is depressible from this initial position to a depressed position corresponding to the approximated position of jaw members 110, 120.

With reference generally to FIGS. 3A-6B, various embodiments of medical devices, some similar to forceps 10, are shown that each include one or more limited-use portions. Generally, these limited-use portions are rendered inoperable during or after the limited-use portions are subjected to sterilization. That is, these limited-use portions may be configured for a single use such that, after being subject to sterilization, the medical devices incorporating such limited-use portions are rendered inoperable. On the other hand, these limited-use portions may be configured to withstand a predetermined number of sterilizations or a pre-determined amount of sterilization such that the medical devices incorporating these limited-use portions may be sterilized and reused until the pre-determined sterilization limit has been reached, at which time the medical devices are rendered inoperable. Further, although the limited-use portions are described below as being incorporated into different components and/or features of a medical device to render the medical device inoperable after sterilization or a pre-determined sterilization limit, it is contemplated that the limited-used portions be incorporated, attached, or otherwise coupled to any suitable component(s) of any suitable medical device for similar purposes.

The sterilization process may include a chemical sterilization procedure. For example, a medical device may be sterilized via chemical sterilization including one or more suitable sterilizing chemicals such as, for example, hydrogen peroxide, water, saline, alcohol, ethylene oxide, ozone, bleach, chlorine, glutaraldehyde, formaldehyde, phthalaldehyde, silver, triclosan, and combinations thereof, and/or via any suitable chemical sterilization procedure such as, for example, STERRAD® sterilization. As a result of such chemical sterilization, the limited-use portion may be compromised, dissolved, destroyed, or the like, due to a chemical reaction caused by the one or more chemicals, or a specific combination of chemicals.

The sterilization process may additionally or alternatively include the use of a radiation sterilization procedure. A medical device may be exposed to radiation, ionizing or non-ionizing, which may degrade the limited-use portion to an inoperable state. The use of any other suitable energy-based sterilization process or processes is also contemplated.

The sterilization process may additionally or alternatively incorporate the use of a high temperature sterilization procedure wherein the medical device is exposed to a sterilization temperature above the degradation temperature of the limited-use portion such that the limited-use portion degrades at the sterilization temperature to render the medical device inoperable.

The sterilization process may additionally or alternatively include the use of an autoclave. More specifically, at least a portion of the medical device may be inserted into the autoclave for sterilization. The autoclave may be capable of dispersing high pressure and sterilization gasses onto the medical device to degrade the limited-use portion thereby rendering the medical device inoperable. The sterilization gasses may include steam, hydrogen peroxide, alcohol, or any other suitable autoclaving or sterilizing fluid or chemical sterilizer as herein described or otherwise known in the art.

Figure 3A:
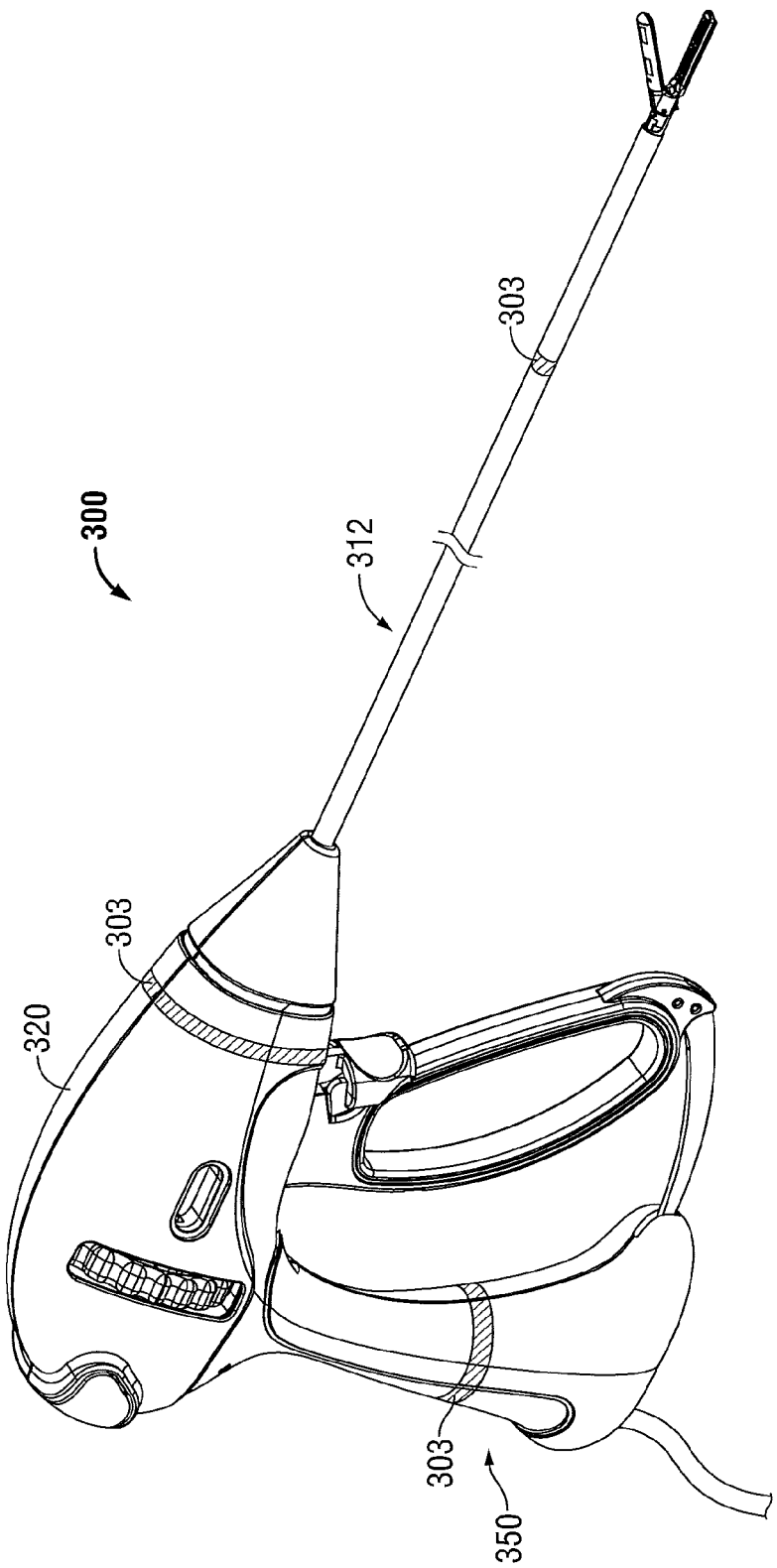
FIG. 3A is a perspective view of another a medical device provided in accordance with the present disclosure, shown before sterilization.
Figure 3B:
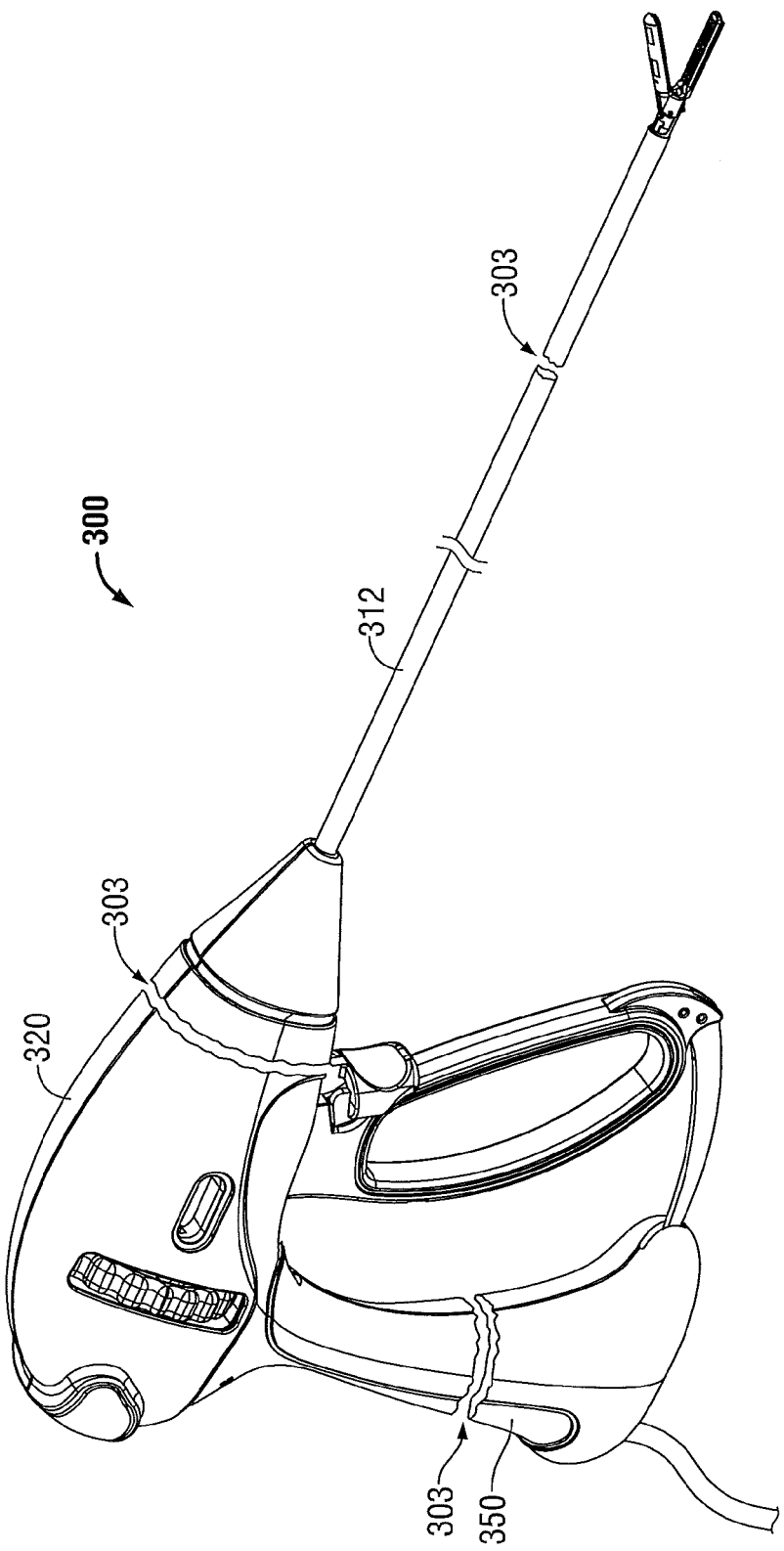
FIG. 3B is a perspective view of the medical device of FIG. 3A, shown after sterilization.

As shown in FIGS. 3A and 3B, the one or more limited-use portions 303 may be incorporated into externally-disposed components or features of a medical device 300. Incorporating limited-use portions 303 into externally-disposed components of medical device 300 is advantageous in that, in addition to rendering one or more components inoperable after the sterilization limit has been reached, the externally-visible limited-use portions 303 provide the user with a clear visual indication that medical device 300 is inoperable and should not be used.

In this embodiment, medical device 300 is similar to medical device 10, described above, and, thus, will not be described in detail herein for purposes of brevity. Limited-use portion 303 may be incorporated into, e.g., formed integrally with or otherwise attached or coupled to, housing 320, shaft 312, fixed handle 350, or any other suitable externally-disposed component of medical device 300.

As shown in FIG. 3B, after sterilization of medical device 300 beyond the pre-determined sterilization limit, one or more limited-use portions 303 of the medical device are at least partially destroyed to the point that the device can no longer mechanically function. For example: where one of the limited-use portions 303 includes a portion of the housing 320, the medical device 300 falls apart and cannot be reassembled; where one of the limited-use portion 303 is part of the handle 350, the device cannot be held properly; and where there is one or more limited-use portions 303 on the shaft 312, the shaft 312 breaks into pieces and cannot be held to the rest of medical device 300.

Figure 3C:
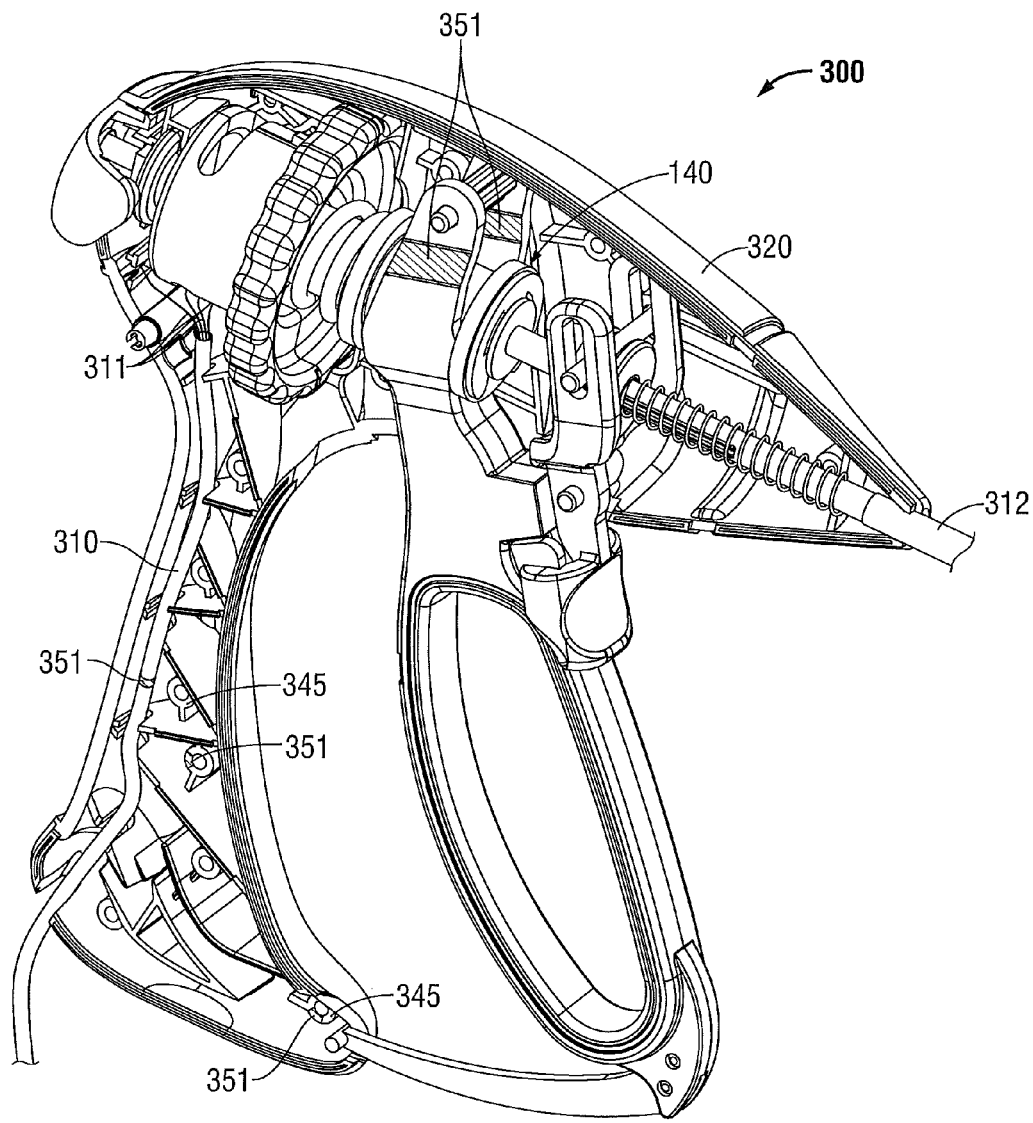
FIG. 3C is a perspective view of an opened half of a housing of a medical device provided in accordance with the present disclosure, shown before sterilization.
Figure 3D:
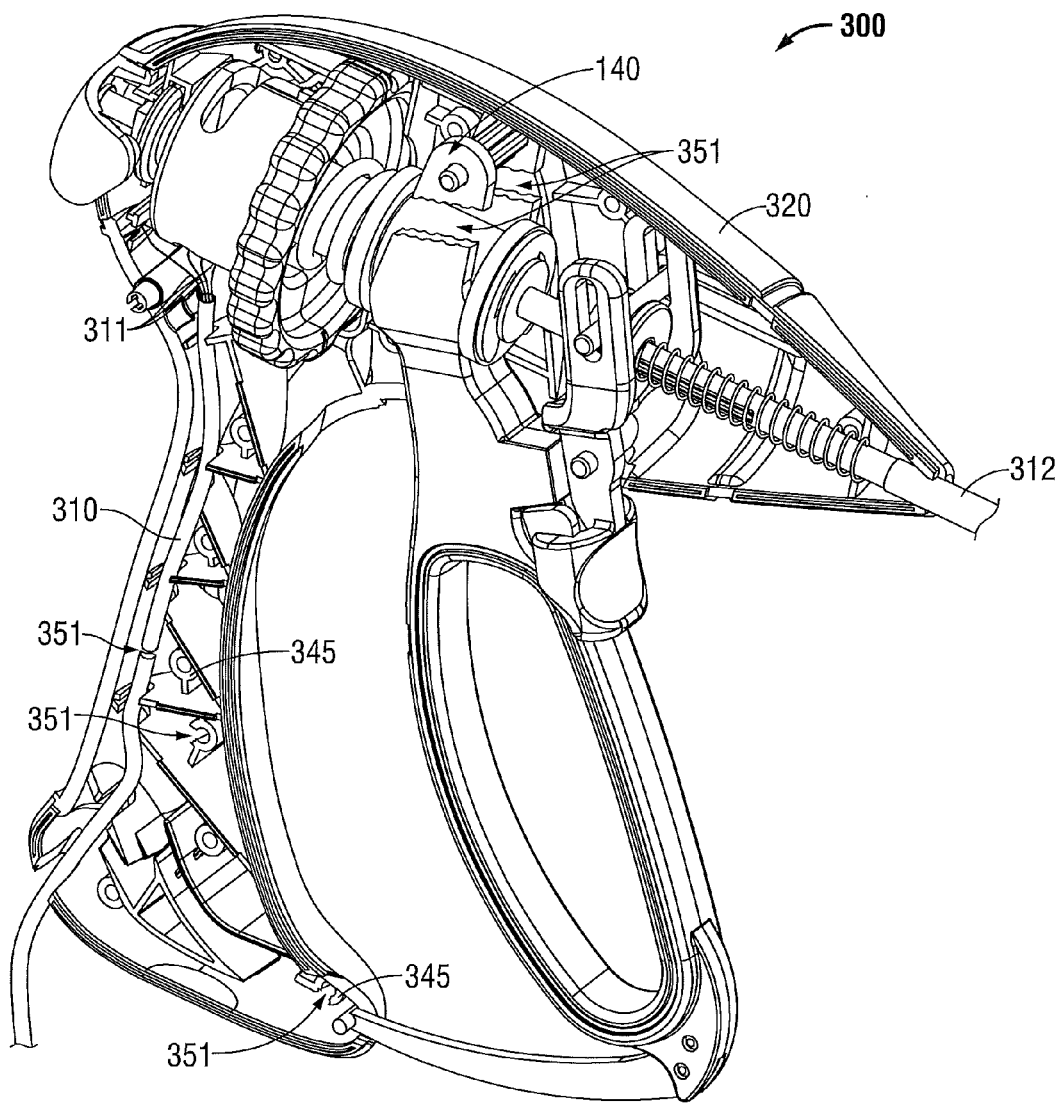
FIG. 3D is a perspective view of the opened half of the medical device of FIG. 3C, shown after sterilization.

As shown in FIGS. 3C and 3D, one or more limited-use portions 351 of medical device 300 may additionally or alternatively be incorporated into internal components or features of medical device 300, such as, but not limited to, snaps 345, cable 310, drive assembly 140, or any other suitable internal feature. With particular reference to FIG. 3D, after the one or more limited-use portions 351 of the medical device 300 are at least partially destroyed, the medical device 300 can no longer mechanically and/or electrically function. For example: where the limited-use portion 351 includes at least a portion of the snaps 345, the medical device 300 falls apart and cannot be reassembled; and where the cable 310 includes one or more limited-use portions 351, the cable 310 is severed at the limited-use portion 351 and can no longer transmit energy.

Figure 4A:
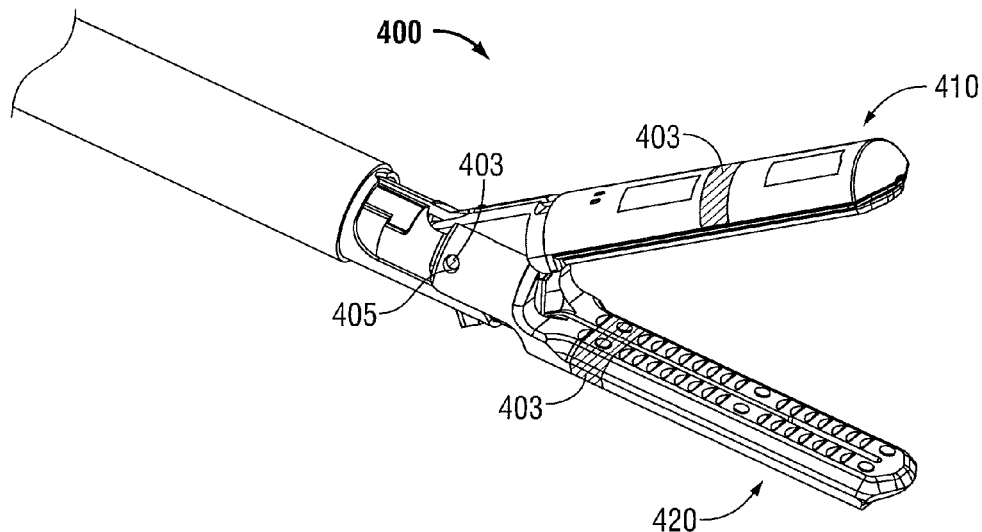
FIG. 4A is a perspective view of an end effector assembly provided in accordance with the present disclosure and configured for use with the medical device of FIG. 1, shown before sterilization.
Figure 4B:
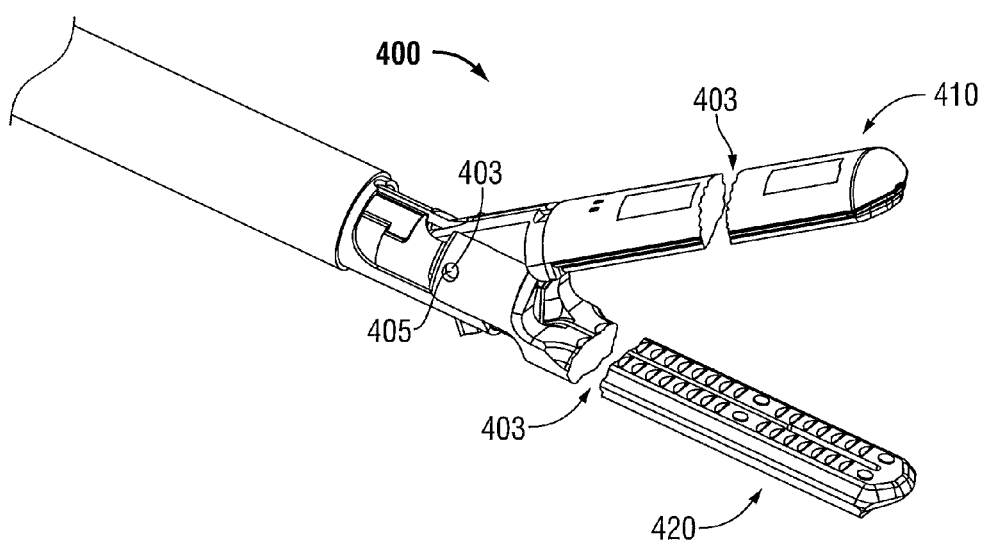
FIG. 4B is an perspective view of the end effector assembly of FIG. 4A, shown after sterilization.

Referring to FIGS. 4A and 4B, an end effector assembly 400 similar to end effector assembly 100 (FIG. 1) and configured for use with forceps 10 (FIG. 1) is shown. End effector assembly 400. As end effector assembly 400 is similar to end effector assembly 100 (FIG. 1), end effector 400 will not be described in detail herein for purposes of brevity. End effector assembly 400 may include one or more limited-use portions 403. Limited-use portions 403, which form structural portions or components of end effector assembly 400, e.g., of either or both of jaw members 410, 420 or portions thereof and/or pivot pin 405 (see FIGS. 4C-4D), are configured such that, once degraded or destroyed, end effector assembly 400 is rendered inoperable.

Figure 4C:
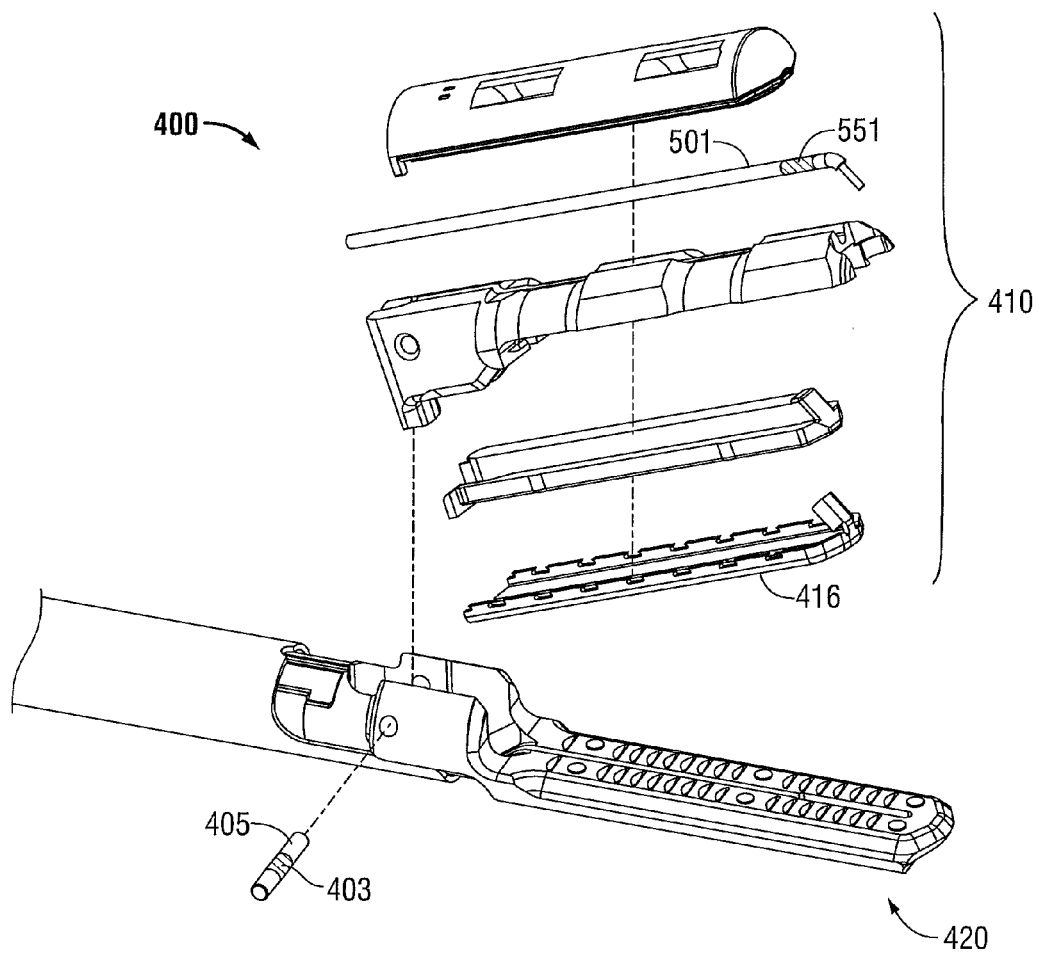
FIG. 4C is an exploded view of another end effector provided in accordance with the present disclosure and configured for use with the medical device of FIG. 1, shown before sterilization.
Figure 4D:
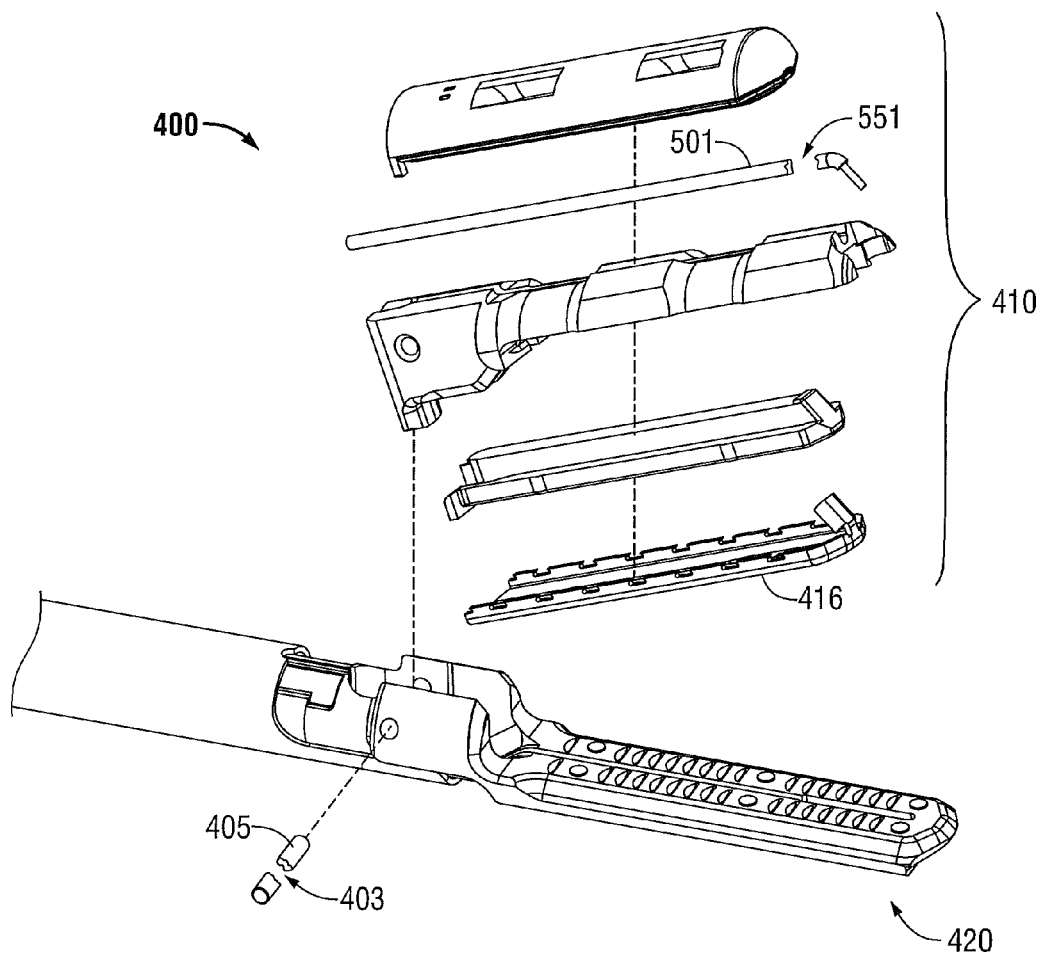
FIG. 4D is an exploded view of the end effector assembly of FIG. 4C, shown after sterilization.

Referring to FIGS. 4C and 4D, end effector assembly 400 may additionally or alternatively include one or more electrical components 501 incorporating a limited-use portion 551 configured to degrade to render the electrical components 501 inoperable after the pre-determined sterilization limit has been reached. Shown in FIG. 5B after the sterilization limit has been reached, electronic component 501, which serves as a lead for providing energy to tissue-contacting surface 416 of jaw member 410, is permanently disconnected, rendering jaw member 410 incapable of receiving energy, thus rendering end effector assembly 400 inoperable. Alternatively or additionally, the lead (not shown) providing energy to jaw member 420 may also incorporate a limited-use portion for similar purposes.

Figure 5A:
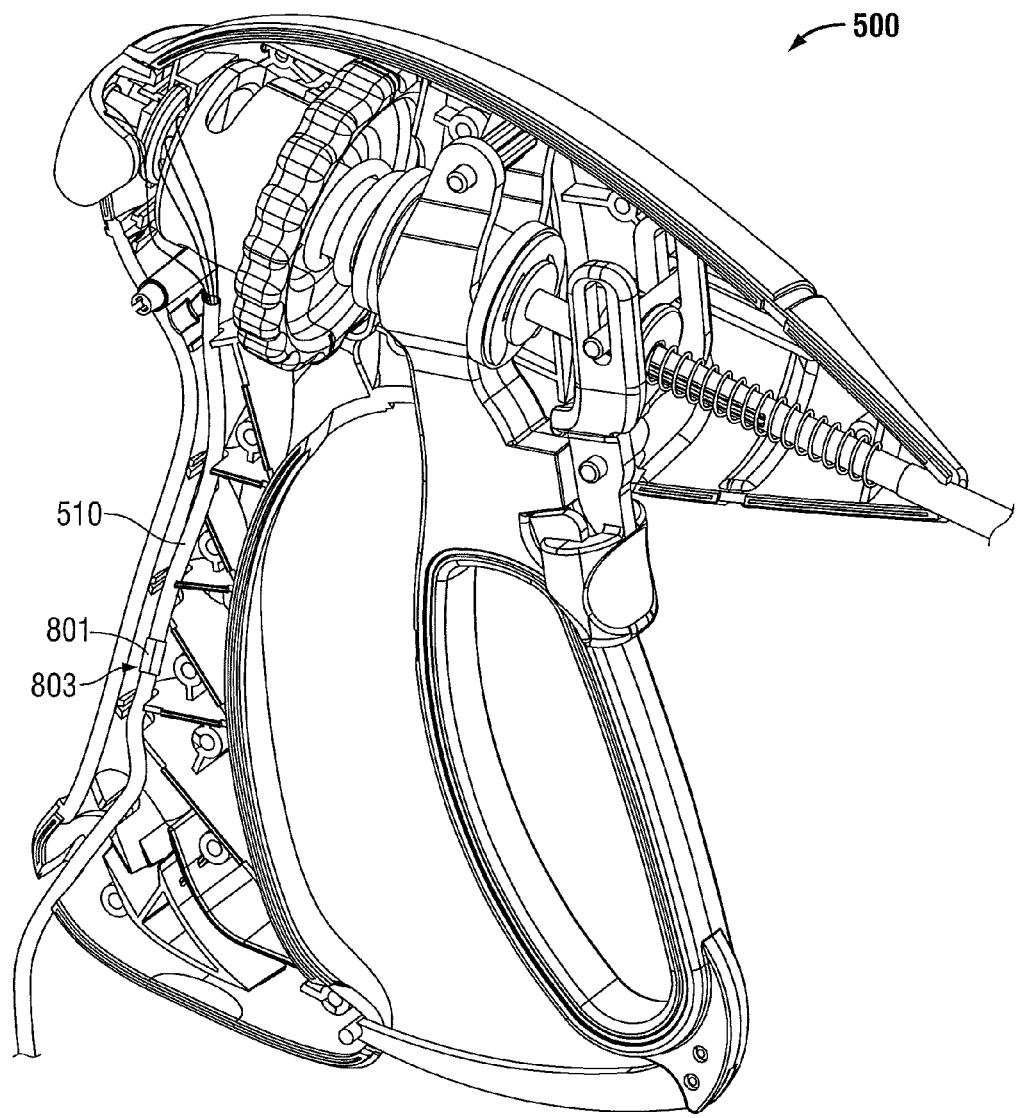
FIG. 5A is a perspective view of an opened half of a housing of a medical device provided in accordance with the present disclosure, shown before sterilization.
Figure 5B:
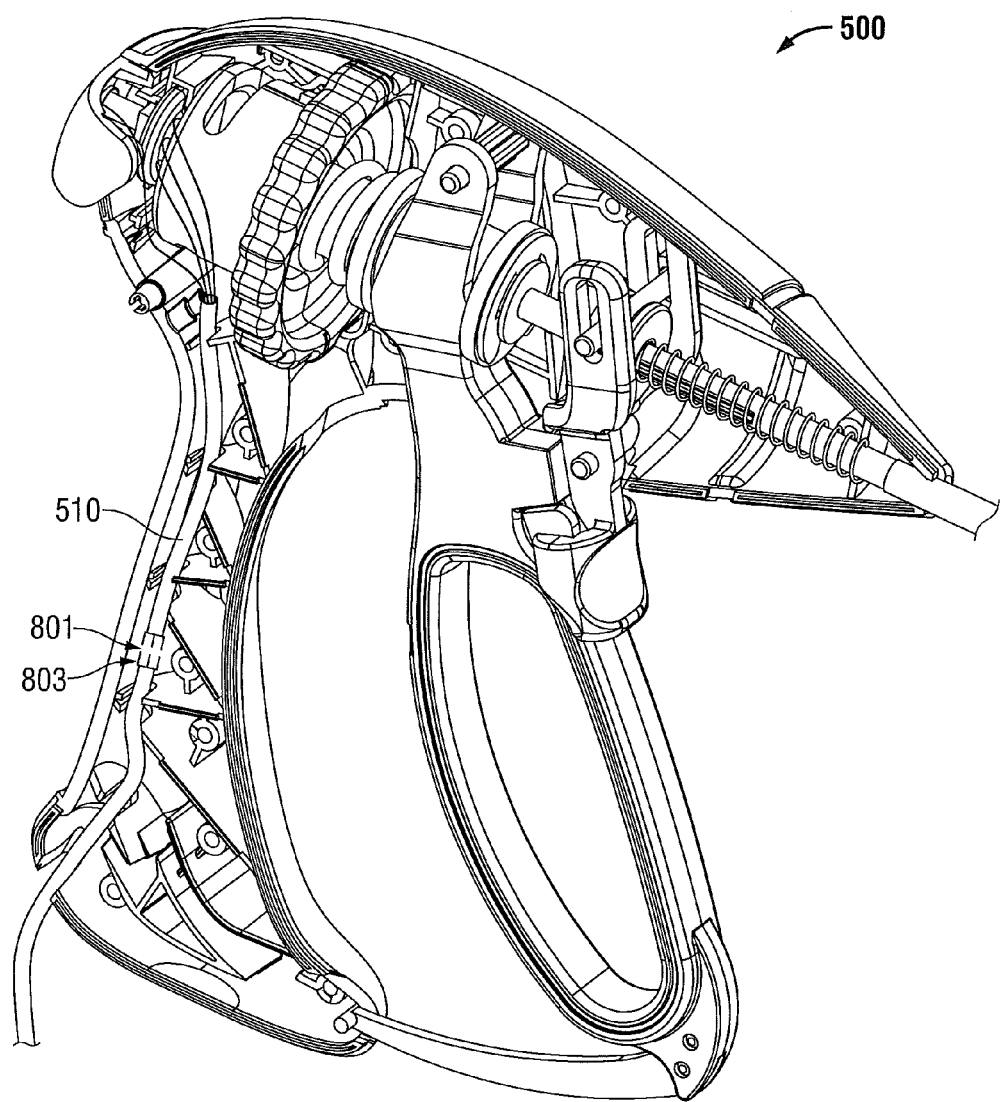
FIG. 5B is a perspective view of the opened half of the medical device of FIG. 5A, shown after sterilization.

Referring to FIGS. 5A and 5B, another medical device 500, similar to forceps 10 (FIG. 1), may include one or more limited-use portions 803 in the form of a temperature fuse 801 that is activated at a sterilization temperature, via sterilization chemicals, or otherwise, to disable cable 510 and disconnect the supply of energy along cable 510, thereby rendering medical device 500 inoperable in that no energy is capable of being transmitted to the end effector assembly (not shown) thereof. A single fuse 801 or multiple fuses 801 may be disposed on any electrical component in device 500, and any combination of fuses 801 on separate electrical systems of medical devices is herein contemplated.

Figure 6A:
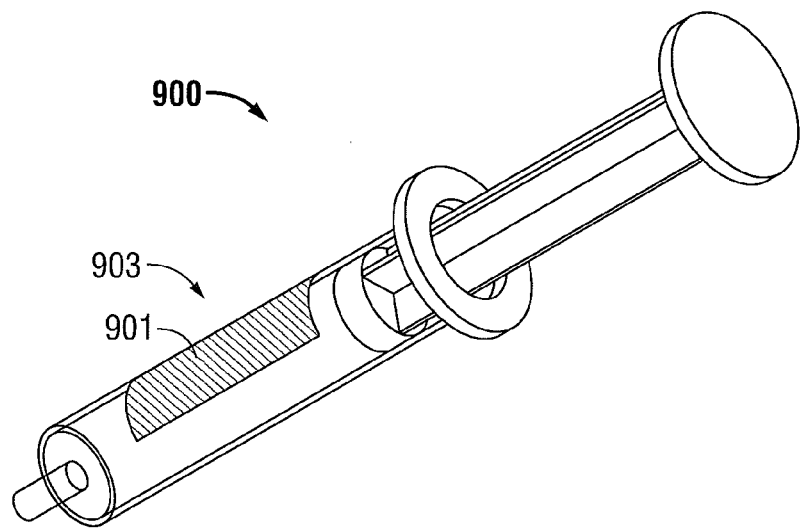
FIG. 6A is a perspective view of a medical device provided in accordance with the present disclosure, shown before sterilization.
Figure 6B:
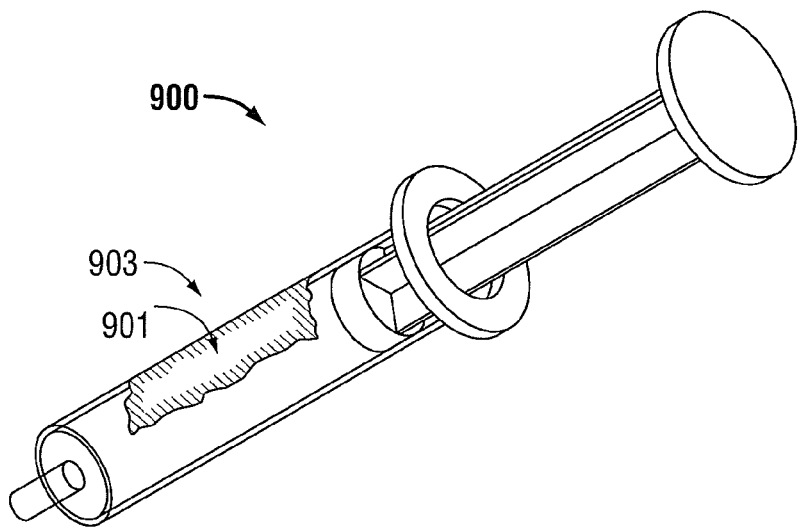
FIG. 6B is a perspective view of the medical device of FIG. 6A, shown after sterilization.

Referring to FIGS. 6A and 6B, another medical device 900 is shown including one or more limited-use portions 903 that has one or more labels 901 that degrades during or after a sterilization procedure. More specifically, identifying features of the label 901 may degrade, rendering the label unidentifiable after sterilization, or the material, e.g., glue, retaining the label 901 on the device 900 may degrade so that the label 901 is not longer attached to the device 900. Label 901 may include any suitable label such as, for example, labels for indicating information and/or characteristics of the medical device 900, labels for identifying and/or tracking the device, e.g., bar code or RFID labels, or labels for any other suitable purpose.

The limited-use portions described herein may be made at least partially from a material that degrades due to the use of any of the sterilization processes described above. For example, the material that degrades may include one or more plastics that deform or melt in an autoclave. The material may be plant-based such that it dissolves through contact with a chemical sterilizer. The material may be radiation or heat-sensitive such that it degrades due to such sterilization. Any suitable materials for these purposes may be provided including, but not limited to, polystyrene, sucrose thermo-plastics selected for melting at a desired heat or chemical exposure, polypropylene or low density polyethylene for UV radiation degradation, and/or ferrous materials to be oxidized by a chemical mixture. Materials that dissolve when wet may also be used, such as, but not limited to, Bakelite (polyoxybenzyl-methylenglycolanhydride), Garolite, polyvinyl alcohol, and combinations thereof. Other suitable materials are also contemplated.

The limited-use portions described herein may include green materials that can be recycled, decompose, or facilitate incineration. In embodiments where the green material is bio-degradable, the green material may be configured to breakdown after a predetermined period of time after first use, exposure to air, e.g., after removal of the instrument from a sealed package, or upon other occurrence. Alternatively, the green material may facilitate incineration.

Through use of the herein described limited use portions, a method of recycling a medical device may be realized. The method may include removing, recycling, or disposing of a limited use portion and reclaiming reusable portions of a medical device. The method may also include sterilizing and/or recycling the reusable portions of the medical device after removal from the medical device.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A medical device, comprising:
   at least one operable component including:
      a housing;
      a pair of jaws coupled to the housing and configured for clamping tissue; and
      at least one electrode connected to the jaws for applying energy to tissue; and
   at least one limited-use portion incorporated into at least one of the housing, the jaws, or the at least one electrode, wherein the limited-use portion is configured to transition from a first state to a second state upon being subjected to sterilization above a sterilization threshold, wherein, in the second state, the at least one limited-use portion is at least one of degraded, dissolved, broken down, or destroyed, to inhibit the operability of the at least one operable component.

2. The medical device of claim 1, wherein sterilization of the limited-use portion above the sterilization threshold renders the medical device mechanically inoperable.

3. The medical device of claim 1, wherein sterilization of the limited-use portion above the sterilization threshold renders the medical device electrically inoperable.

4. The medical device of claim 1, wherein sterilization includes use of a chemical sterilization process, and wherein the limited-use portion is sensitive to at least one chemical used in the chemical sterilization process.

5. The medical device of claim 4, wherein the chemical sterilization process includes the use of at least one chemical sterilizer selected from the group consisting of hydrogen peroxide, water, saline, alcohol, ethylene oxide, ozone, bleach, chlorine, glutaraldehyde, formaldehyde, phthalaldehyde, silver, and triclosan, and wherein the limited-use portion is configured to at least one of degrade, dissolve, break down, or destruct due to contact with at least one of the at least one chemical sterilizers.

6. The medical device of claim 1, wherein sterilization includes use of an autoclave, and wherein the limited-use portion is configured to at least one of degrade, dissolve, break down, or destruct due to autoclaving.

7. The medical device of claim 1, wherein sterilization includes the use of at least one energy-based sterilization process, and wherein the limited-use portion is configured to at least one of degrade, dissolve, break down, or destruct due to exposure to the at least one energy-based sterilization process.

8. The medical device of claim 1, wherein sterilization includes a high temperature sterilization process having a sterilization temperature, and wherein the limited-use portion is configured to at least one of degrade, dissolve, break down, or destruct at a temperature equal to or below the sterilization temperature.

9. The medical device of claim 8, wherein the limited-use portion further includes at least one temperature fuse connected to at least one electrical component of the at least one operable component, the temperature fuse configured to at least one of degrade, dissolve, break down, or destruct at a temperature equal to or below the sterilization temperature.

10. A method, comprising:
    subjecting at least one of a handle assembly, a shaft, or an end effector of a medical device to sterilization above a sterilization threshold, thereby transitioning a limited-use portion of at least one of the handle assembly, the shaft, or the end effector of the medical device from a first state to a second state, wherein, in the second state, the at least one limited-use portion is at least one of degraded, dissolved, broken down, or destroyed to inhibit the operability of at least one operable component of the medical device.

11. The method of claim 10, wherein sterilization of the medical device above the sterilization threshold renders the medical device mechanically inoperable.

12. The method of claim 10, wherein sterilization of the medical device above the sterilization threshold renders the medical device electrically inoperable.

13. The method of claim 10, wherein sterilization includes a chemical sterilization process, and wherein the limited-use portion transitions to the second state due to contact with at least one chemical used in the chemical sterilization process.

14. The method of claim 10, wherein sterilization includes the use of an autoclave, and wherein the limited-use portion transitions to the second state due to autoclaving.

15. The method of claim 10, wherein sterilization includes at least one energy-based sterilization process, and wherein the limited-use portion transitions to the second state due to exposure to the at least one energy-based sterilization process.

16. The method of claim 10, wherein sterilization includes a high temperature sterilization process including a sterilization temperature, and wherein the limited-use portion transitions to the second state at a temperature equal to or below the sterilization temperature.

17. A medical device, comprising:
a handle assembly;
a shaft extending distally from the handle assembly;
an end effector coupled to a distal end of the shaft; and
at least one limited-use portion incorporated into at least one of the handle assembly, the shaft, or the end effector, wherein the limited-use portion is configured to at least one of degrade, dissolve, break down, or destruct during or after the limited-use portion is subjected to sterilization.

18. The medical device according to claim 17, wherein the limited-use portion is fabricated from at least one of polystyrene, sucrose thermo-plastics, polypropylene, low density polyethylene, ferrous materials, polyoxybenzylmethylengly-colanhydride, or polyvinyl alcohol.

\* \* \* \* \*